United States Patent [19]

Koyama et al.

[11] Patent Number: 4,495,358

[45] Date of Patent: Jan. 22, 1985

[54] ANTIBIOTIC PYRROLOMYCIN E

[75] Inventors: Masao Koyama, Yokohama; Takashi Tsuruoka, Kawasaki; Norio Ezaki, Yokohama; Keinosuke Miyauchi, Yokohama; Shigeharu Inouye, Yokohama, all of Japan

[73] Assignee: Meiji Seika Kaisha, Ltd., Tokyo, Japan

[21] Appl. No.: 438,658

[22] Filed: Nov. 2, 1982

[30] Foreign Application Priority Data

Dec. 23, 1981 [JP] Japan ............................. 56-206967

[51] Int. Cl.³ .................... C07D 205/10; A61K 31/40
[52] U.S. Cl. .................................................. 548/550
[58] Field of Search ......................................... 548/550

Primary Examiner—Richard Raymond
Assistant Examiner—D. B. Springer
Attorney, Agent, or Firm—Ladas & Parry

[57] ABSTRACT

Antibiotic, designated as pyrrolomycin E is described, and which is obtained by cultivating an pyrrolomycin E - producing strain belonging to the genus Streptomyces, for example, Streptomyces sp. SF-2080 (FERM-P No. 5072, ATCC No. 31673), in a nutrient medium, and recovering pyrrolomycin E from the culture which contains also other antibiotic substances (pyrrolomycin A, B, C and D) together with the desired substance.

2 Claims, 2 Drawing Figures

ANTIBIOTIC PYRROLOMYCIN E

BACKGROUND OF THE INVENTION

This invention relates to a novel antibiotic now designated as pyrrolomycin E and a process for production of the same. More particularly it relates to a novel antibiotic pyrrolomycin E which is obtained by cultivating an pyrrolomycin E-producing strain belonging to the genus Streptomyces in a nutrient medium and recovering the antibiotic pyrrolomycin E so produced from the culture, and to a process for producing the antibiotic pyrrolomycin E.

The substrate mycelium is abundantly branched and stretches in a wave-form. The diameter of the hypha is 0.5 to 0.6 micron. Usually, no fragmentation of the substrate mycelium is observed in either agar culture medium or liquid medium. Aerial mycelium is not formed on the usually used agar culture medium. Spore, sporangium, zoospore, sclerotium, coremia, etc., have not yet been observed.

(II) Culture Characteristics:

The observation was carried out after cultivation at 28° C. for 14 days, according to the method as described in E. B. Shirling & D. Gottlieb, International Journal of Systematic Bactoriology, Vol. 16, pp. 313–340 (1966).

The culture and growth characteristics with respect to various media are shown in the following Table 1.

TABLE 1

| Culture Medium | Growth and Reverse Color | Aerial Mycelium | Soluble Pigment |
| --- | --- | --- | --- |
| Sucrose-Nitrate Agar | Very scant growth, colorless | None | Not produced |
| Glucose-Asparagine Agar | Very scant growth, colorless | None | Not produced |
| Glycerol-Asparagine Agar | Scant growth, colorless | None | Not produced |
| Calcium Malate Agar | Very scant growth, colorless | None | Not produced |
| Starch Agar | Very scant growth, colorless | None | Not produced |
| Yeast Malt Agar | Moderate growth, in a thin skin form, colorless to light yellowish brown | None | Not produced |
| Tyrosine Agar | Scant to moderate growth, colorless to light yellowish brown | None | Not produced |
| Nutrient Agar | Moderate growth, light yellowish brown | None | Not produced |
| Oatmeal Agar | Scant to moderate growth, colorless | None | Not produced |
| Bennett's Agar | Moderate growth, colorless to light yellowish brown | None | Not produced |

It has been found that a pyrrolomycin E-producing strain may produce pyrrolomycin E together with other antibiotics; SF-2080 A, B, C and D respectively named pyrrolomycin A, B, C and D.

SUMMARY OF THE INVENTION

This invention provides a novel antibiotic designated pyrrolomycin E, and a process for producing pyrrolomycin E by cultivating a pyrrolomycin E-producing strain belonging to the genus Streptomyces in a nutrient medium.

DETAILED DESCRIPTION OF THE INVENTION

Figure 1:
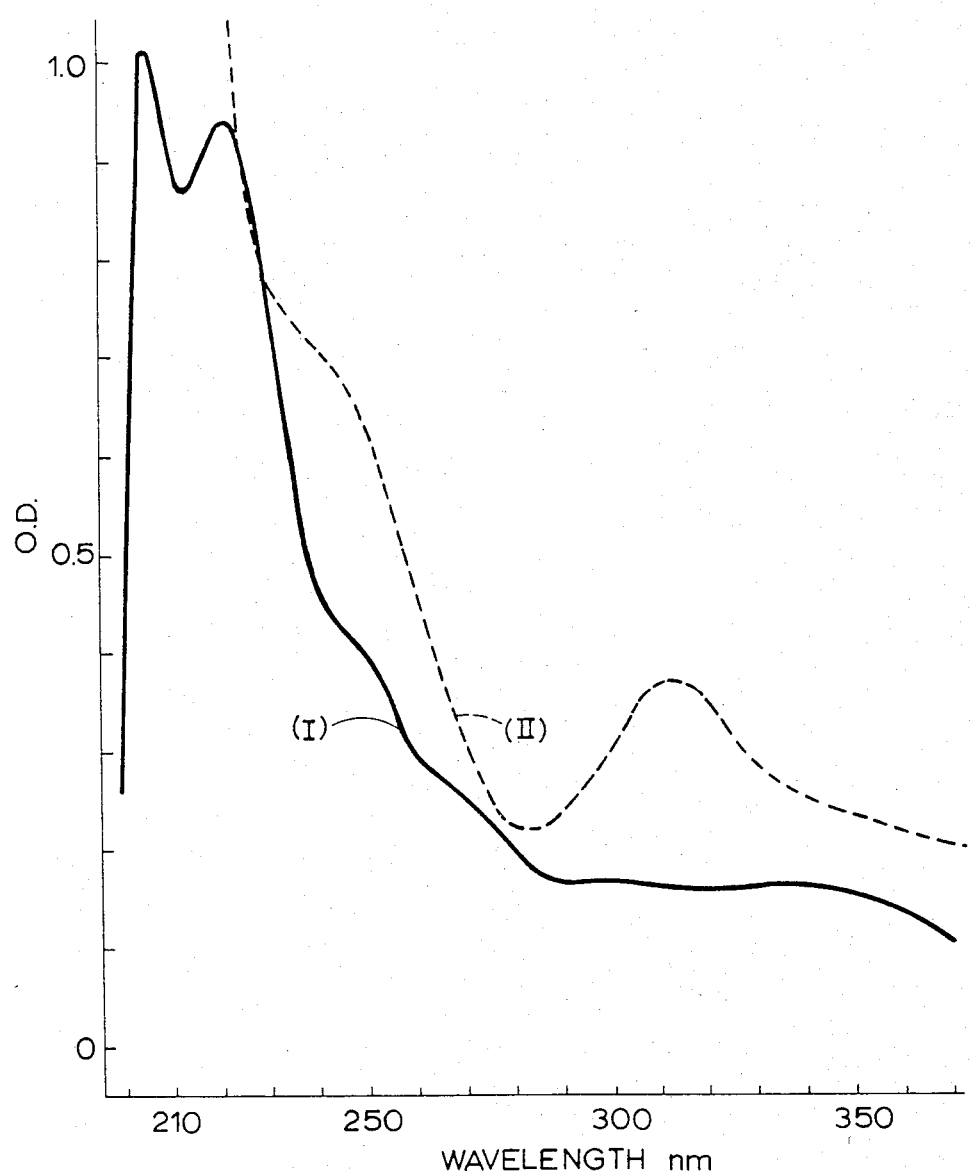
FIG. 1 is an ultraviolet absorption spectrum of pyrrolomycin E as measured at a concentration of 10.9 mcg/ml (micrograms/milliliter) in (I) neutral methanol, (II) alkaline methanol.

Any strain capable of producing the antibiotic pyrrolomycin E in an amount sufficient to be recovered from the fermentation broth can be used as the antibiotic pyrrolomycin E-producing strain in this invention. An example of such strains is Streptomyces sp. SF-2080 which is also capable of producing antibiotics SF-2080 A, B, C and D respectively named pyrrolomycin A, B, C and D (See; J. Antibiotics (1981). P.1363; Preliminary Patent Publication No. 90099/1981 (Japan); Preliminary Patent Publication No. 56492/1982 (Japan); Preliminary Patent Publication No. 53494/1982 (Japan)).

The Streptomyces sp. SF-2080 has been isolated from a soil sample collected from the riverbed of River Chikuma in Nagano-city, Nagano Prefecture, Japan and the characteristics of which are as follows:

(I) Morphological Characteristics:

(III) Physiological Characteristics:

(1) Growth Temperature Range: Grows in yeast malt agar at a range of from 15° C. to 45° C., and grows well at from 25° C. to 34° C.

(2) Liquefaction of Gelatin: Positive (cultivation at 20° C. for 21 days).

(3) Hydrolysis of Starch: Positive (weak, cultivation at 28° C. for 14 days).

(4) Action on Skim Milk: Neither peptonization nor coagulation occurs on cultivation at 28° C. for 14 days.

(5) Reduction of Nitrate: Positive (cultivation at 28° C. for 14 days).

(6) Salt Resistance: Growth occurs at 1.5%, but not at 3.0%.

(7) Production of Melanine-Like Pigment: Negative (IV) Utilization of Carbon Sources:

As Streptomyces sp. SF-2080 can not grow on Pridam-Gottlieb medium, a basic culture medium consisting of 0.5% of yeast extract (Difco), 0.1% of calcium carbonate and 1.5% of agar (Difco) was employed to examine the utilization of carbon sources. The results are shown in Table 2.

TABLE 2

| Carbon Source | Growth* |
| --- | --- |
| D-Glucose | + |
| D-Xylose | + |
| D-Fructose | − |
| L-Arabinose | − |
| D-Mannitol | − |
| i-Inositol | − |
| L-Rhamnose | + |
| Sucrose | − |
| Raffinose | − |

*Symbol "+" means utilizable.
Symbol "−" means not utilizable.

(V) Composition of Cell Wall:

Analysis according to Becker, et al., Appl. Microbiol., Vol. 13, p. 236 (1965) showed that diaminopimelic acid contained in the cell wall composition is of LL type.

From the above characteristics, it was judged that Streptomyces sp. SF-2080 belongs to the order Actinomycetales and is a mesophilic, which shows no fragmentation of the substrate mycelium and which contains LL-diaminopimelic acid in the cell wall.

It is, however, not possible at the present time to conclusively determine the genus to which the SF-2080 strain belongs because such morphological characteristics as spare, sporangium, zoospore, sclerotium and coremia which are necessary for determination of the genus of actinomycetes have not yet been made clear.

However, taking into account the fact that the SF-2080 strain contains LL-diaminopimelic acid in the cell wall, the present inventors tentatively consider for the present that the SF-2080 strain is an unidentified species belonging to the genus of Streptomyces, and therefore named it Streptomyces sp. SF-2080.

This strain has been deposited as Streptomyces sp. SF-2080 in the Fermentation Research Institute, Agency of Industrial Science and Technology, Ministry of International Trade and Industry of Japan under the accession number of FERM-P No. 5072 and in the American Type Culture Collection under ATCC number 31673.

The SF-2080 strain easily varies in its properties as in the case with other actinomycetes strains. Such variation can be caused artificially by irradiating with ultraviolet rays, X-rays, high frequency waves or radioactive rays, and by chemicals.

Therefore, all variants as well as mutants can be used in the process of this invention so long as they have the ability to produce the antibiotic pyrrolomycin E.

In accordance with the process of this invention, the above-described strain is cultivated in a medium containing nutrients which are assimilable by known microorganisms. Such nutrients are known materials conventionally used in cultivation of actinomycetes strains. Examples of carbon sources include glucose, glycerin, sucrose, starch, dextrin, maltose syrup, molasses, soybean oil, etc. Examples of nitrogen sources include soybean meal, wheat germ, cottonseed meal, meat extract, peptone, yeast extract, dry yeast, corn steep liquor, ammonium sulfate, sodium nitrate, etc. Additionally, if desired, inorganic salts such as calcium carbonate, sodium chloride, cobalt chloride, phosphates, etc., as well as organic and inorganic material which help the growth of microorganisms and enhance microbial production of pyrrolomycin E can appropriately be used.

The submerged cultivation method under aerated condition is most suitable for cultivation of the pyrrolomycin E-producing strain as is for the case with the production of known antibiotics. The suitable temperature range for the cultivation is from 25° C. to 34° C., and, preferably at 28° C. to 32° C. The production of pyrrolomycin E reaches a maximum in from 2 to 7 days in both shake-culture and tank-culture, and pyrrolomycin E is accumulated in the cultivation broth filtrate and my celia (solid matter).

The determination of pyrrolomycin E can be carried out by a combination of the bioassay using Sarcine lutea as a test organism and thin layer chromatography using silicagel.

Pyrrolomycin E has physical and chemical properties as hereinafter described. According to these properties, it can be extracted and purified. The following method can be efficiently used:

To a filtrate obtained by filtering off solid matter from a culture broth containing the desired substance is added an organic solvent which is not freely miscible with water, such as ethyl acetate, etc. They are then stirred to extract the desired substance.

On the other hand, an organic solvent which is freely miscible with water, such as acetone, methanol, etc., is added to the solid matter and stirred to extract the desired substance therefrom. After evaporating off the organic solvent, the desired substance is extracted with an organic solvent such as ethyl acetate, etc.

Extracts from the broth filtrate and the solid matter are combined. The solvent is evaporated to obtain an oily substance. The oily substance is subjected to a well-known purification method such as column chromatography using organic solvents and recrystallization, etc. to isolate and crystalize the desired substance, pyrrolomycin E. The crystals of pyrrolomycin E, when analyzed by thin layer chromatography using various solvent systems, provides a single spot, which indicates that it is a pure product.

The physical and chemical properties and the minimum inhibitory concentration against various microorganisms as measured by agar dilution method of pyrrolomycin E as obtained by the above-described method are as follows:

TABLE 3

| | | | |
|---|---|---|---|
| 1. Elemental Analysis | C: 39.10%; N: 8.94% | H: 1.61%; Cl: 34.88% | |
| 2. Molecular Weight | 306 | | |
| 3. Molecular Formula | $C_{10}H_5N_2O_3Cl_3$ | | |
| 4. Melting Point | above 250° C. (decomposition) | | |
| 5. Optical Rotation | $[\alpha]_D^{25} = 0$ (C = 0.5, methanol) | | |
| 6. Ultraviolet Absorption Spectrum | Shown in FIG. 1. | | |
| 7. Infrared Absorption Spectrum | Shown in FIG. 2 The characteristic absorption bands, as determined using the potassium bromide tablet method, are 3320, 1560, 1475, 1380, 1290, 1045 cm$^{-1}$. | | |
| 8. Color Reaction | Positive: Negative: | Iodine reaction and Lemieux reaction Ninhydrin reaction | |
| 9. Appearance and Color of the Substance | Yellow needle-shaped crystals. Weak acidic substance | | |
| 10. Rf Value on Thin Layer Chromatography (Silicagel, 60 F 254, E. Merck) | 0.60 (benzene-ethyl acetate-acetic acid (100:20:1)) | | |
| 11. Solubility | Soluble in methanol, acetone, ethyl acetate, sparingly soluble in water, n-hexane | | |
| 12. Structural Formula | 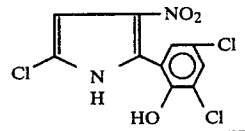 | | |

TABLE 4

| Test Organism | Minimum Inhibitory Concentration (mcg/ml) |
|---|---|
| Staphylococcus aureus FDA209PJC-1 | 1.56 |
| Staphylococcus aureus Smith | 1.56 |
| Staphylococcus epidermidis ATCC 14990 | 1.56 |
| Bacillus subtilis ATCC 6633 | 0.025 |
| Escherichia coli NIHJ JC-2 | >100 |
| Escherichia coli W 3630 RGN823 | 12.5 |
| Salmonella typhi 0-901-W | >100 |
| Klebsiella pneumoniae PCI-602 | >100 |
| Proteus vulgaris OX-19 | 6.25 |
| Serratia marcescens No. 1 | >100 |

TABLE 4-continued

| Test Organism | Minimum Inhibitory Concentration (mcg/ml) |
|---|---|
| *Pseudomonas aeruginosa* IAM 1007 | >100 |

By comparing the physical and chemical properties and biological characteristics of pyrrolomycin E with those of the known antibiotics, it was found that it is a novel antibiotic. The acute toxicity of the pyrrolomycin E was measured by intraperitoneal administration in mice, and the mice were observed for a week. All mice survived at a dose of 10 mg/kg. The pyrrolomycin E is therefore useful as medicines, animal medicines, sterilizing agents, etc.

The following examples are given to illustrate this invention in detail. It is to be noted that many modifications and variations can be made without departing from the scope of this invention.

EXAMPLE

A liquid medium of a composition comprising 2% of glucose, 0.5% of peptone, 0.3% of yeast extract, 0.2% of soybean meal, 0.2% of meat extract and 0.1% of calcium carbonate was prepared. Then, 20 ml portions of the liquid medium so prepared were separately introduced into a 100 ml Erlenmeyer flask and sterilized. Streptomyces sp. SF-2080 (FERM-P No. 5072, ATCC No. 31673) was inoculated in the liquid medium and incubated on a shaker at 28° C. for 5 days to prepare First Seed Culture. The same procedure as above was repeated, the volume being gradually increased, to prepare Second and Third Seed Culture.

35 l of a culture medium having the composition comprising 2% of maltose syrup, 0.15% of soybean oil, 1% of soybean meal, 0.25% of distiller's solubles, 0.5% of Fermamedia (trademark, produced by Traders Oil Mill Co., Texas), 0.0005% of ferrous sulfate, 0.00005% of nickel chloride, 0.00005% of cobalt chloride and 0.1% of calcium carbonate was charged into a 50 l stainless steel fermentation tank, sterilized and then inoculated with 800 ml of the Third Seed Culture.

The cultivation was carried out at 28° C. while aerating and stirring. The amount of aeration and rotation speed were 35 l/minute and 300 rpm respectively.

After a period of 120 hours, the cultivation was stopped and the culture was separated into a solid fraction and a filtrate by filtration. 20 l of ethyl acetate was added to 25 l of the filtrate and stirred to extract the effective component. Then, the ethyl acetate layer was separated.

10 l of a 50% aqueous acetone was added to the solid fraction and stirred to extract the effective component. The solid fraction was then filtered off. Thereafter, the filtrate was concentrated under reduced pressure to evaporate acetone and then, 2.5 l of ethyl acetate was added and stirred to extract the effective component. Thereafter, the ethyl acetate layer was separated and combined with the ethyl acetate extraction layer from the filtrate. The resulting mixture was concentrated under reduced pressure to obtain about 30 ml of tarry substance.

To the tarry substance was added 180 ml of benzene and 100 ml of water, followed by the addition of 5% sodium bicarbonate to adjust the pH to 7.5. The benzene layer was separated and dehydrated with anhydrous sodium sulfate. The dehydrated benzene layer was subjected to 180 g column of basic alumina whereby to adsorb the effective substance therein. Upon the addition of ethyl acetate into the alumina column, the fractions containing pyrrolomycin E was eluted after the fractions containing pyrrolomycin A. Pyrrolomycin B, C and D were remained in the column. The fractions containing pyrrolomycin E were combined and concentrated under reduced pressure, thereby obtaining 20 mg of yellowish crystalline substance. By the recrystallization from a mixture of benzene-ethyl acetate, 88 mg of purified crystals were obtained, which showed a melting point of above 250° C. (decomposition).

Figure 2:
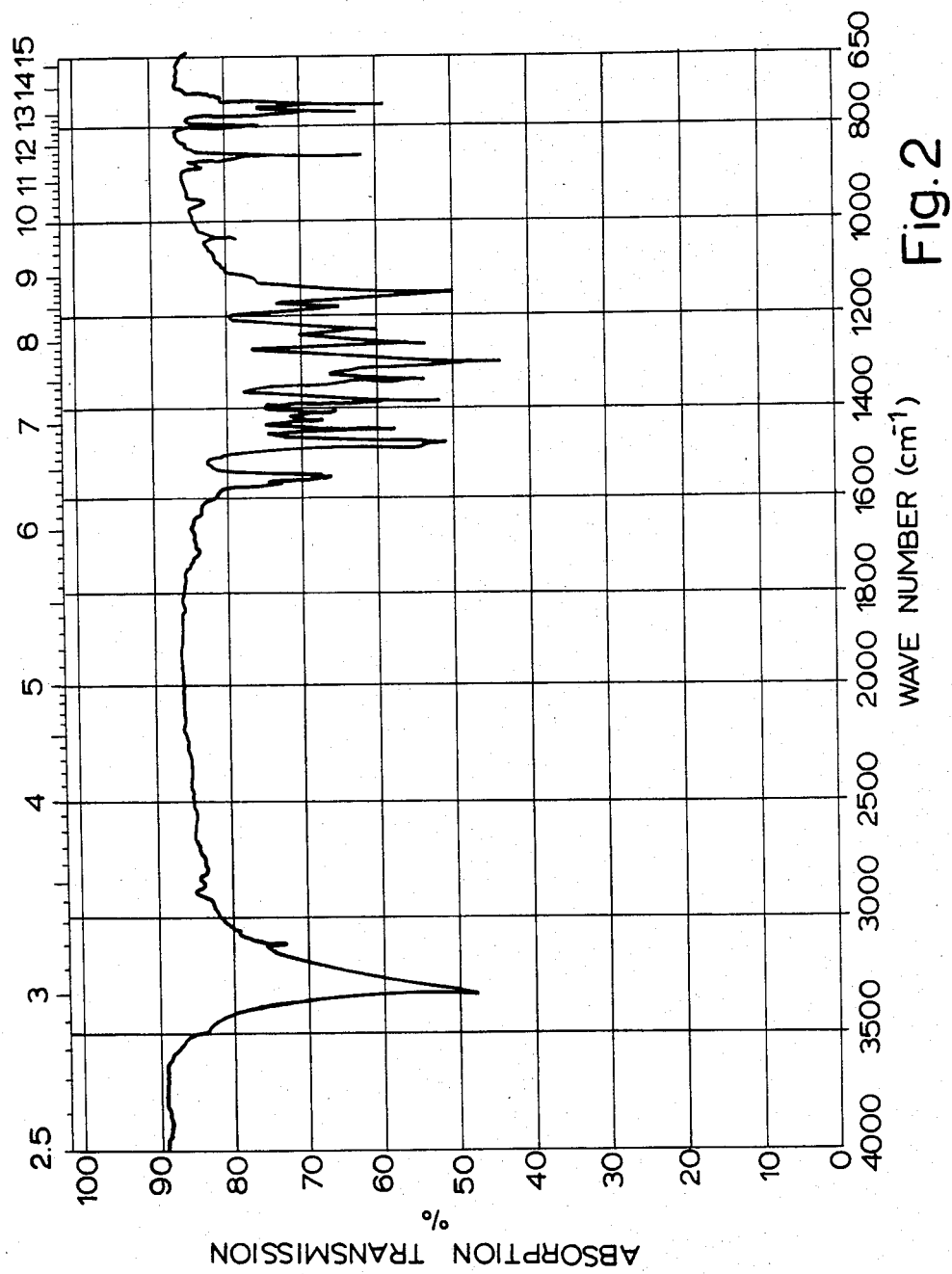
FIG. 2 is an infrared absorption spectrum of pyrrolomycin E as measured in a potassium bromide tablet.

What is claimed is:

1. An antibiotic, pyrrolomycin E having the following properties:
   Elementary Analysis (by weight): C, 39.10%, H, 1.61%; N, 8.94%; Cl, 34.88%;
   Molecular Weight: 306;
   Molecular Formula: $C_{10}H_5N_2O_3Cl_3$;
   Melting Point: above 250° C. (decomposition);
   Optical Rotation: $[\alpha]_D^{25}=0$ (C=0.5, methanol);
   Ultraviolet Absorption Spectrum: as shown in FIG. 1;
   Infrared Absorption Spectrum: as shown in FIG. 2;
   The characteristic absorption bands, as determined using the potassium bromide tablet method, are 3320, 1560, 1475, 1380, 1290, 1045 cm$^{-1}$;
   Color Reaction: Positive for the iodine reaction and Lemieux reaction, and negative for the ninhydrin reaction;
   Appearance and Color: Yellow needle-shaped crystals (weak acidic substance);
   Rf Value on Thin Layer Chromatography (silicagel, 60F254, E. Merck): 0.6 (benzene-ethyl acetate-acetic acid (100:20:1));
   Solubility: Soluble in methanol, acetone, ethyl acetate, sparingly soluble in water, n-hexane.

2. An antibiotic pyrrolomycin E with a structural formula:

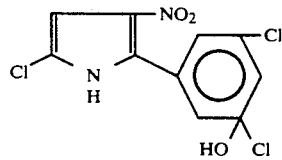

* * * * *